United States Patent
Tsuyuki et al.

(10) Patent No.: US 9,778,211 B2
(45) Date of Patent: Oct. 3, 2017

(54) X-RAY CT (COMPUTED TOMOGRAPHY) DEVICE

(71) Applicant: Toshiba Medical Systems Corporation, Otawara-shi (JP)

(72) Inventors: Masaharu Tsuyuki, Nasushiobara (JP); Toshiyuki Shinno, Sakura (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/742,705

(22) Filed: Jan. 16, 2013

(65) Prior Publication Data

US 2013/0182821 A1  Jul. 18, 2013

(30) Foreign Application Priority Data

Jan. 16, 2012 (JP) ................... 2012-005849

(51) Int. Cl.
*A61B 6/03* (2006.01)
*G01N 23/04* (2006.01)
*A61B 6/00* (2006.01)

(52) U.S. Cl.
CPC ......... *G01N 23/046* (2013.01); *A61B 6/032* (2013.01); *A61B 6/482* (2013.01); *A61B 6/56* (2013.01); *G01N 2223/419* (2013.01)

(58) Field of Classification Search
CPC ............ G01N 23/046; G01N 2223/419; A61B 6/032; A61B 6/482
(Continued)

(56) References Cited

U.S. PATENT DOCUMENTS 5,272,627 A * 12/1993 Maschhoff ............... H04N 5/32
                                                                    378/4
5,568,530 A * 10/1996 Saito et al. .................. 378/4
(Continued)

FOREIGN PATENT DOCUMENTS

CN         1765327 A      5/2006
CN       101229063 A      7/2008
(Continued)

OTHER PUBLICATIONS

Combined Chinese Office Action and Search Report issued Aug. 1, 2014 in Patent Application No. 201310016380.3.
(Continued)

*Primary Examiner* — Glen Kao
(74) *Attorney, Agent, or Firm* — Oblon, McClelland, Maier & Neustadt, L.L.P.

(57) ABSTRACT

As one embodiment, the X-ray CT device comprises an X-ray tube, a tube voltage generator, an X-ray detector, a data accumulating unit, and an image processing unit. The tube voltage generator applies tube voltage to the X-ray tube. The tube voltage controlling unit controls the tube voltage generator so as to periodically alternate the tube voltage. The X-ray detector is arranged across a subject from the X-ray tube, and detects the X-rays penetrating the subject. The data accumulating unit accumulates first sampling data when a high voltage is applied to said X-ray tube in one cycle by synchronizing with the change in said tube voltage from the data detected by said X-ray detector, and after a predetermined amount of time has passed from said accumulation, accumulates second sampling data when a low voltage is applied to said X-ray tube. The image processing unit creates images based on the accumulated first sampling data and second sampling data.

3 Claims, 12 Drawing Sheets

(58) Field of Classification Search
USPC .............................................. 378/16, 19, 21
See application file for complete search history.

(56) References Cited

U.S. PATENT DOCUMENTS

| | | | |
|---|---|---|---|
| 7,209,537 B2 * | 4/2007 | Popescu ........................... | 378/16 |
| 7,471,757 B2 * | 12/2008 | Tsukagoshi et al. ............. | 378/4 |
| 2006/0109951 A1 * | 5/2006 | Popescu ................. | A61B 6/032 |
| | | | 378/4 |
| 2008/0144764 A1 | 6/2008 | Nishide et al. | |
| 2009/0092219 A1 | 4/2009 | Wu et al. | |
| 2009/0097611 A1 * | 4/2009 | Nishide ................. | A61B 6/032 |
| | | | 378/5 |
| 2009/0135994 A1 * | 5/2009 | Yu et al. ........................... | 378/5 |
| 2009/0180585 A1 | 7/2009 | Fujimoto et al. | |
| 2009/0214095 A1 * | 8/2009 | Wu ......................... | G06T 5/002 |
| | | | 382/131 |
| 2010/0303196 A1 | 12/2010 | Zou | |
| 2011/0158380 A1 * | 6/2011 | Tsukagoshi et al. ............. | 378/4 |

FOREIGN PATENT DOCUMENTS

| | | |
|---|---|---|
| CN | 101897595 A | 12/2010 |
| JP | 58-41531 A | 3/1983 |
| JP | 63-203137 A | 8/1988 |
| JP | 2008-279153 | 11/2008 |
| JP | 2009-95405 A | 5/2009 |
| JP | 2009-131464 A | 6/2009 |
| JP | 2009-297442 A | 12/2009 |
| JP | 2010-167165 A | 8/2010 |
| JP | 2010-284350 A | 12/2010 |

OTHER PUBLICATIONS

Office Action issued Oct. 13, 2015 in Japanese Patent Application No. 2012-005849.

Office Action issued Jun. 20, 2016, in Chinese Application No. 201310016380.3.

Office Action dated Jun. 6, 2017 in Japanese Patent Application No. 2016-146635.

* cited by examiner

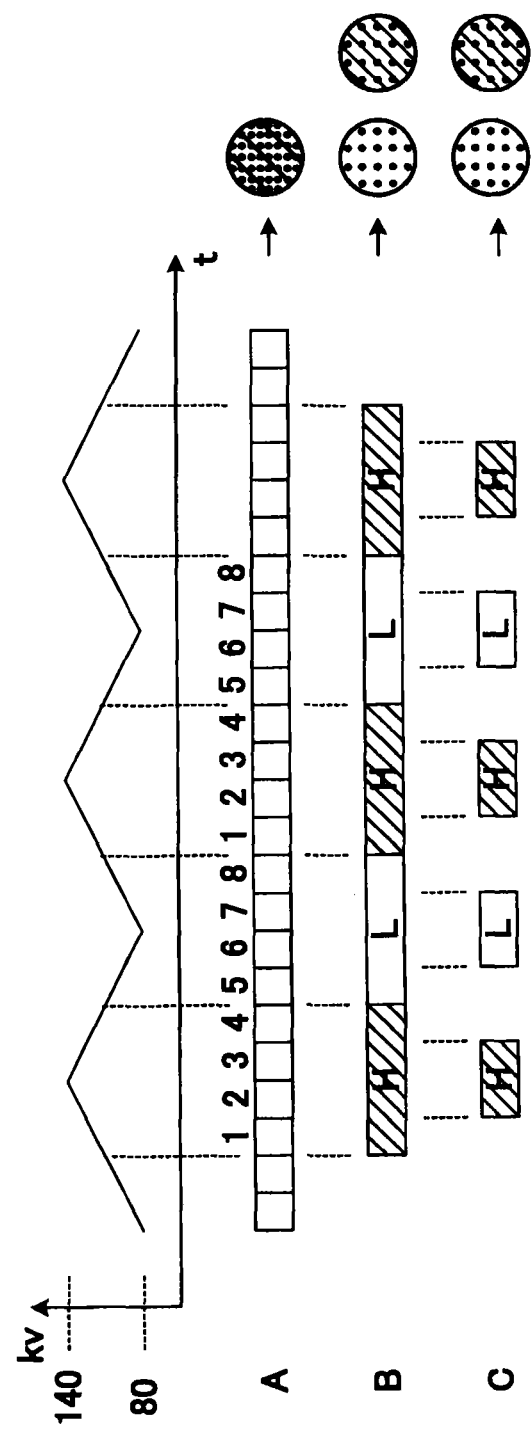

X-RAY CT (COMPUTED TOMOGRAPHY) DEVICE

CROSS-REFERENCE TO RELATED APPLICATION

This application is based upon and claims the benefit of priority from Japanese Patent Application No. 2012-005849, filed Jan. 16, 2012; the entire contents of which are incorporated herein by reference

FIELD

The embodiment of the present invention relates to an X-ray CT device.

BACKGROUND

The X-ray CT device carries out X-ray photography while an X-ray tube and an X-ray detector arranged facing each other with a subject on a top plate rotate around the subject.

By means of X-ray photography, data (CT value) on the subject is accumulated, and characteristics of the subject are diagnosed based on the CT value.

The CT value is expressed by a "mass attenuation coefficient"*"density". The "mass attenuation coefficient" is a value peculiar to substances. Accordingly, depending on the density state of the substance, there are times in which there is no difference in the CT value even when the substances are different, and which it is difficult to discriminate the substance based on the CT value.

The CT Dual Energy Scan method accumulates data on a subject using different tube voltages as a means of solving such phenomenon. The accumulated data may be referred to as projection data, accumulated data, or raw data.

This method includes a dual-source method, Photon Counting method, and rapid kV switching method.

One example of the rapid kV switching method accumulates data while switching the tube voltage per 1 view between a high voltage (140 kV) and a low voltage (80 kV). The switching frequency of the tube voltage may be referred to as the switching cycle.

The view count per one rotation is proportional to the resolution of the image; therefore, in order to obtain a high resolution tomographical image, the switching cycle must be shortened accordingly when the revolving speed is fast.

However, there is limit to the switching cycle regarding the rapid kV switching method; wherein, if the revolving speed is fast, the switching cycle cannot be shorted accordingly, resulting in problems of the view count per one rotation being insufficient, not being able to obtain sufficient resolution, and not being able to obtain high resolution tomographical images.

The present embodiment solves the abovementioned problems with the purpose of providing an X-ray CT device that obtains high resolution tomographical images by obtaining sufficient resolution even when the revolution speed is fast.

BRIEF DESCRIPTION OF THE DRAWINGS

FIG. 12 is an image respectively showing an example in which the change in tube voltage becomes a triangle wave, a storing example of all oversampled data A, a comparative bundling example B, and a bundling example C regarding Embodiment 4.

DETAILED DESCRIPTION

The X-ray CT device of the embodiment comprises an X-ray tube, a tube voltage generating means, an X-ray detector, a data accumulating means, and an image processing means. The tube voltage generating means applies a tube voltage to the X-ray tube. The tube voltage controlling means controls the tube voltage generating means so as to periodically alternate the tube voltage. The X-ray detector is arranged across a subject from the X-ray tube, and detects the X-rays penetrating the subject. The data accumulating means accumulates first sampling data when a high voltage is applied to the X-ray tube in one cycle by synchronizing with the change in the tube voltage from the data detected by the X-ray detector, and after a predetermined amount of time has passed from the accumulation, accumulates second sampling data when low voltage is applied to the X-ray tube. The image processing means creates images based on the accumulated first sampling data and second sampling data.

Embodiment 1

A fundamental configuration of Embodiment 1 of said X-ray CT device is described with reference to FIG. 1.

Figure 1:
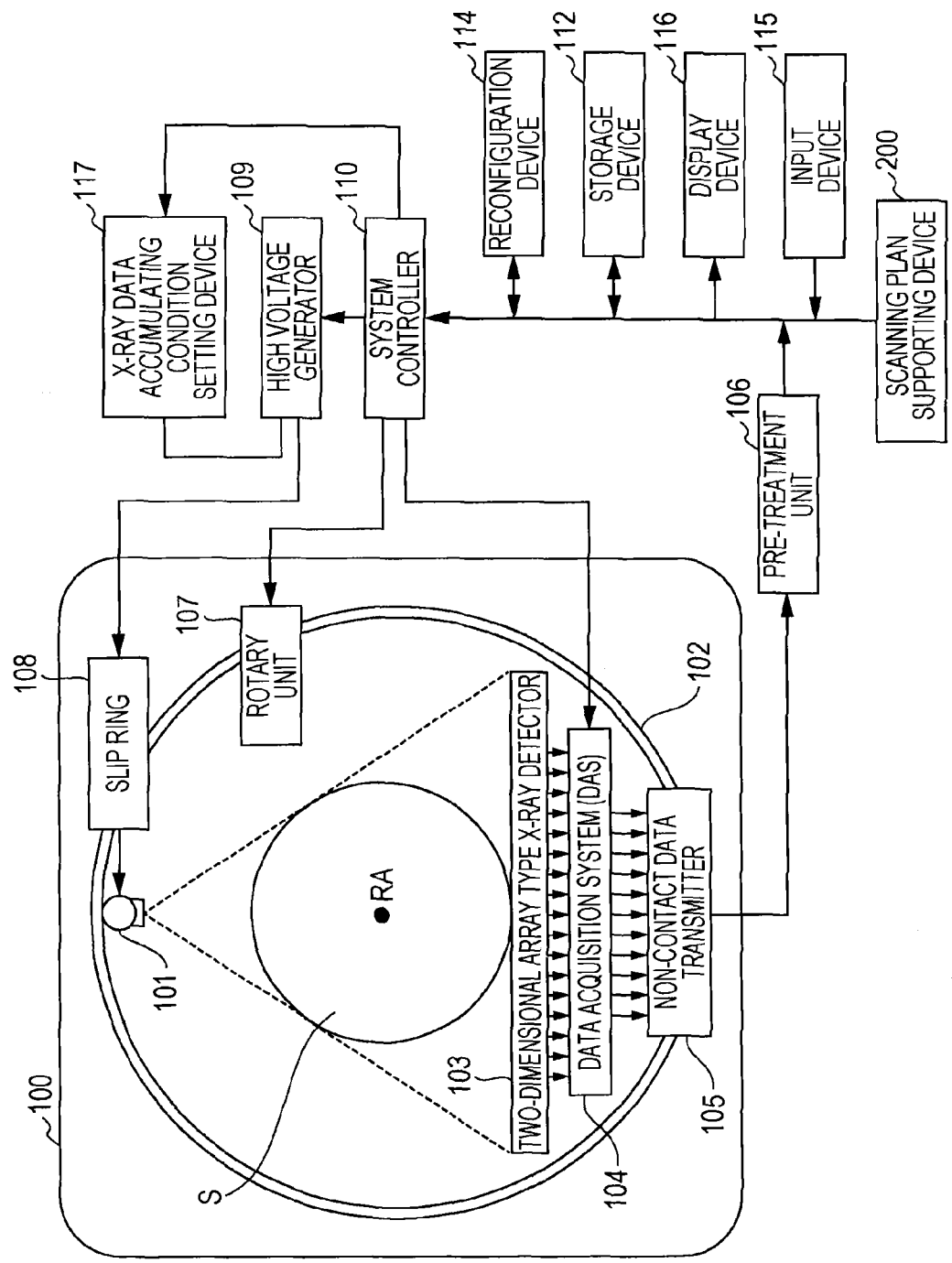
FIG. 1 is a configuration block diagram of the X-ray CT device.

As shown in FIG. 1, the X-ray CT device comprises a gantry 100. The gantry 100 comprises an X-ray tube 101, a multiple-array type or a two-dimensional array type X-ray detector 103, and a data acquisition system (DAS) 104.

The X-ray tube 101 and the X-ray detector 103 are mounted on an annular frame 102 provided around a rotation axis RA allowing for rotation. The X-ray detector 103 is arranged facing the X-ray tube 101.

The system controller 110 controls a rotary unit 107, thereby rotating a frame 102 at high speeds of 0.4 seconds/rotation, etc. The system controller 110 controls a moving unit (not illustrated), thereby shifting a top plate (not illustrated). By means of shifting the top plate, a subject S loaded on the top plate is shifted along the rotation axis RA.

The high voltage generator 109 applies tube voltage to the X-ray tube 101 in order to generate X-rays from the X-ray tube 101, in addition to supplying a filament current. The system controller 110 controls the high voltage generator 109 so as to periodically alternate the tube voltage of the X-ray tube 101 between a high voltage (for example, 140 kV) and a low voltage (for example, 80 kV). Furthermore, the high voltage and low voltage may be referred to as a high energy level and a low energy level.

A DAS 104 converts signals output from the X-ray detector 103 of respective channels to voltage signals, amplifies the voltage signals thereof, and further converts these into digital signals.

The system controller 110 is connected with an X-ray data accumulating condition setting device 117, a pre-treatment unit 106, a storage device 112, a reconfiguration device 114, an input device 115, a display device 116, and a scanning plan supporting device 200 by a data/controlling bus.

The X-ray data accumulating condition setting device 117 sets the tube voltage and tube current such that noise from the data of different tube voltages becomes similar or of a constant ratio when the tube voltage of the X-ray tube 101 is different; in addition, it corresponds to the respective tube voltages and sets conditions (accumulation conditions) such as rest time, view count, etc. of X-ray accumulation of the DAS 104

The system controller 110 receives input by means of an input device 115 and sets accumulation conditions with respect to the X-ray data accumulating condition setting device 117. Based on said accumulation conditions, the system controller 110 controls the high voltage generator 109 so as to periodically alternate the tube voltage per 1 view in addition to synchronizing with the change thereof and controlling the DAS 104 so as to collect data. Furthermore, the details on data accumulation are described later.

The data output from the DAS 104 is transmitted to the pre-treatment unit 106 housed in a console via a non-contact data transmitter 105. The pre-treatment unit 106 revises the uniformity in sensitivity between channels with respect to raw data, and moreover, revises excessive declines in signal strength or signals due to an X-ray intensity absorber (mainly the metal part). The revised data output from the pre-treatment unit 106 is transmitted to the storage device 112. Furthermore, the data output from the DAS 104 may be referred to as raw data. Moreover, the data output from the pre-treatment unit 106 may be referred to as projected data. Furthermore, output of the data (raw data, projected data) may be referred to as data accumulation.

The storage device 112 stores the data (projected data) that underwent various revisions by the pre-treatment unit 106 together with supplementary information including view identification numbers.

The reconfiguration device 114 receives pretreated projected data and reconstructs images based on said projected data. The projected data undergoes fast fourier transform (FFT), and is converted to a frequency domain; then, three-dimensional back projection processing is carried out with respect to the project data processed by overlapping a reconfiguration function, and a tomographical image is obtained for each anteroposterior direction of the subject S.

The reconfiguration device 114 comprises a two-dimensionally distributed tomographical image of X-ray tube voltage-dependent data involved in the distribution of atoms from both the high voltage and low voltage projected data, a so-called dual energy image reconstruction reconstructing the tomographical image from dual energy photography. Furthermore, the image processing means comprises the reconfiguration device 114.

The display device 116 converts the obtained tomographical image into display data, then displays this on a display.

The scanning plan supporting device 200 comprises a function of supporting a camera operator in scheduling a scanning plan.

The fundamental configuration of the X-ray CT device was described in the above.

(Data Accumulation)

Next, data accumulation is described with reference to FIG. 2 and FIG. 3.

Figure 2:
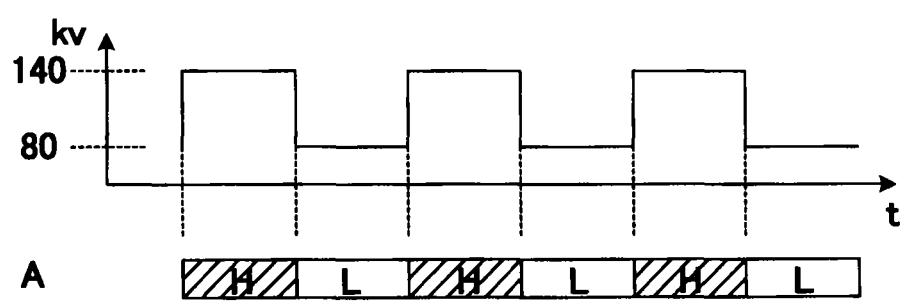
FIG. 2 is an image respectively showing an example in which the change in tube voltage becomes a rectangular wave and a data accumulation example regarding a comparative example.

FIG. 2 is an image respectively showing an example in which the change in tube voltage becomes a rectangular wave, as well as data accumulation example A. The tube voltage exhibited in FIG. 2 indicates time [t] on the horizontal axis, voltage [kV] on the vertical axis, and in the example A, the high voltage and low voltage data accumulation are shown as "H" and "L." Furthermore, the tube voltage periodically alternates between high voltage and low voltage per 1 view based on the switching cycle. The same is applied regarding the following comparative example and embodiment.

As shown in FIG. 2, the high voltage and low voltage data accumulations "H" and "L" are continuously carried out within 1 cycle.

In contrast, the data is accumulated as follows in Embodiment 1. FIG. 3 is an image respectively showing an example in which the change in tube voltage becomes a rectangular wave and data accumulation example A. In the example A of FIG. 3, the high voltage, low voltage, and medium voltage data accumulation are shown as "H," "L," and "M."

Figure 3:
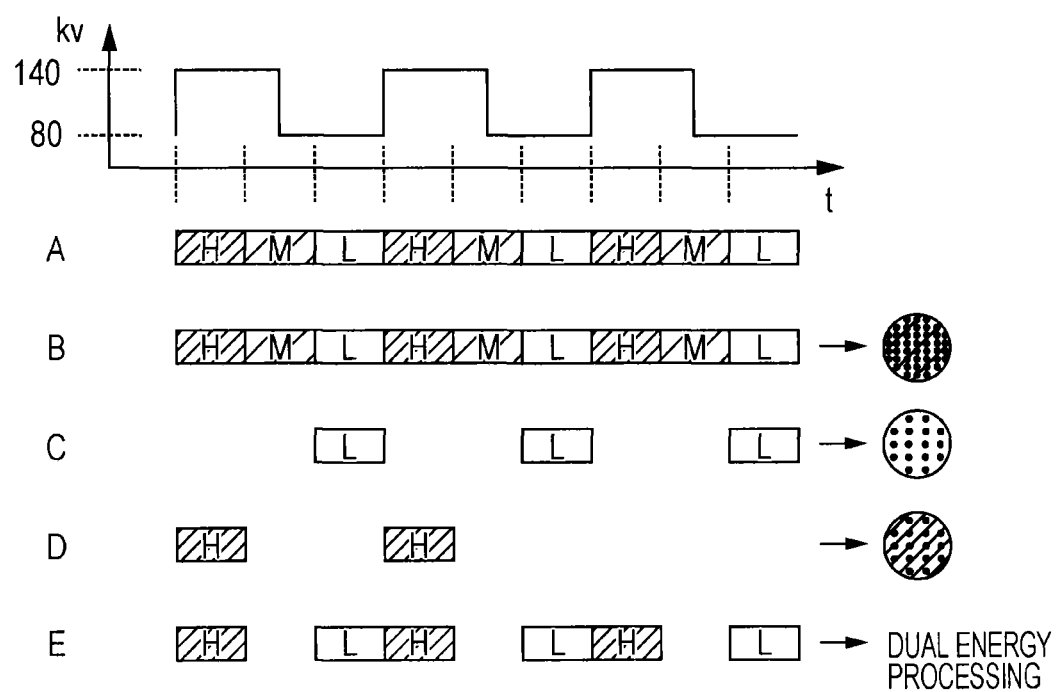
FIG. 3 is an image respectively showing an example in which the change in tube voltage becomes a rectangular wave, data accumulation example A, image reconstruction examples B to D, and decomposition process example E.

As shown in the example A of FIG. 3, the system controller 110 transmits the prepared rectangular waves to the high voltage generator 109, thereby controlling the high voltage generator 109 such that the tube voltage periodically alternates per 1 view in addition to transmitting control signals for instructing data accumulation to the DAS 104, thereby carrying out high voltage data accumulation "H" within 1 cycle by synchronizing with the change in tube voltage, controlling the DAS 104 so as to carry out low voltage data accumulation "L" after the predetermined amount of time has past from said accumulation "H." Furthermore, the predetermined amount of time may be referred to as an open period.

Furthermore, the system controller 110 controls the DAS 104 so as to carry out data accumulation "M" when a medium voltage is applied to the X-ray tube 101 within the predetermined amount of time (open period). Here, the data accumulated in "H," "L," and "M," respectively, may be referred to as first sampling data, second sampling data, and third sampling data. The same is applied regarding the description of the embodiment explained later.

Furthermore, though a case of carrying out data accumulation 3 times in 1 cycle was exhibited, this may be carried out 4 times or more. Furthermore, accumulations expressed as "H," "L," and "M" may be respectively assigned to each trial.

(Image Processing)

Next, image processing using the data accumulated by the DAS 104 is described with reference to FIG. 3. FIG. 3 is an image respectively showing image reconstruction examples B to D, along with decomposition process example E.

As shown in example B of FIG. 3, the reconfiguration device 114 reconstructs the tomographical images using all from the first sampling data to the third sampling data.

Furthermore, by means of using all sampling data, it becomes data of an average energy (medium energy). Thereby, a medium-energy single energy image with high resolution may be obtained.

As shown in example C of FIG. 3, the reconfiguration device 114 reconstructs the tomographical images using the second sampling data. Thereby, a low-energy single energy image may be obtained.

As shown in example D of FIG. 3, the reconfiguration device 114 reconstructs the tomographical images using the first sampling data. Thereby, a high-energy single energy image may be obtained.

As shown in example E of FIG. 3, the reconfiguration device 114 carries out dual energy processing using the first sampling data and second sampling data. Here, the dual energy processing includes substance separation and single color image processing. Here, substance separation refers to photographing an object with a mixture of several substances, calculating the density of the mixed substances, and obtaining the image of a particular object extracted from the mixing ratio of the several substances. Moreover, single color image processing refers to multiplying a mass attenuation coefficient with respect to respective X-ray effective energies and the calculated respective substance density, then remixing the respective substances on the image, thereby obtaining an equivalent CT image of virtual monochromatic X-rays photographed with the respective X-ray effective energies.

According to the abovementioned Embodiment 1, when photographing with a plurality of energies, both dual energy processing and high resolution may be achieved even when the rotation speed is fast.

Moreover, in the example in which the change in tube voltage becomes rectangular waves, the excessive voltage value is taken when the tube voltage switches over from a high voltage to a low voltage; however, there is a possibility that the data from this area may not be revised, etc., yielding a problem of not being able to obtain high resolution tomographical images in the event of occurrence of artifacts. However, in Embodiment 1, the predetermined amount of time (open period) was provided for data accumulation, so the data of said area is excluded, thereby eliminating the cause of the occurrence of artifacts, and allowing high resolution tomographical images to be obtained. Furthermore, this effect is the same regarding the following embodiment.

Furthermore, Embodiment 1 showed a case of accumulating data photographed with three types of energies for the first sampling data, the second sampling data, and the third sampling data within 1 cycle by synchronizing with the change in tube voltage; however, the first sampling data and the second sampling data alone may be accumulated without accumulating the data photographed with medium energy (third sampling data). At this time, the amount of time for accumulating third sampling data becomes a predetermined amount of time (open period); therefore, as mentioned above, the predetermined amount of time (open period) was provided in data accumulation, so the data of said area is excluded, thereby eliminating the cause of the occurrence of artifacts. Furthermore, this configuration and effect is the same regarding the following embodiment.

Embodiment 2

Next, Embodiment 2 is described with reference to FIG. 4 and FIG. 5. Furthermore, in Embodiment 2, configurations differing from Embodiment 1 are mainly described, with descriptions of the same configuration abbreviated.

Figure 4:
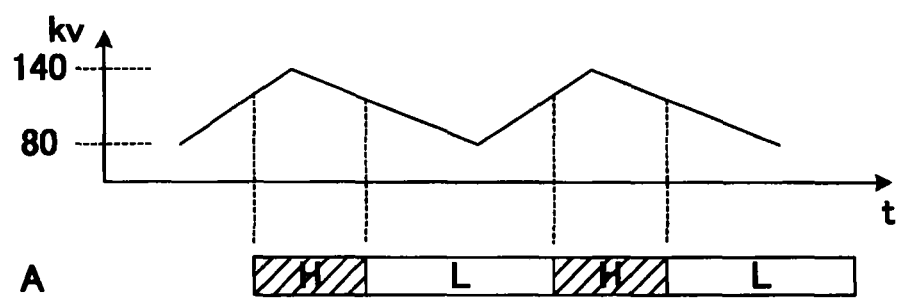
FIG. 4 is an image respectively showing an example in which the change in tube voltage becomes a triangle wave and a data accumulation example regarding the comparative example.

FIG. 4 is an image respectively showing an example in which the change in tube voltage becomes a triangle wave and an example A of data accumulation regarding the comparative example.

(Data Accumulation)

As shown in FIG. 4, in the data accumulation within 1 cycle, the first sampling data accumulation "H" and the second sampling data accumulation "L" are consecutive.

In contrast, data accumulation is carried out as follows in Embodiment 2. FIG. 5 is an image respectively showing an example in which the change in tube voltage becomes a triangle wave and data accumulation example A. In the example A of FIG. 5, the high voltage, low voltage, and medium voltage data accumulation are expressed as "H," "L," and "M."

Figure 5:
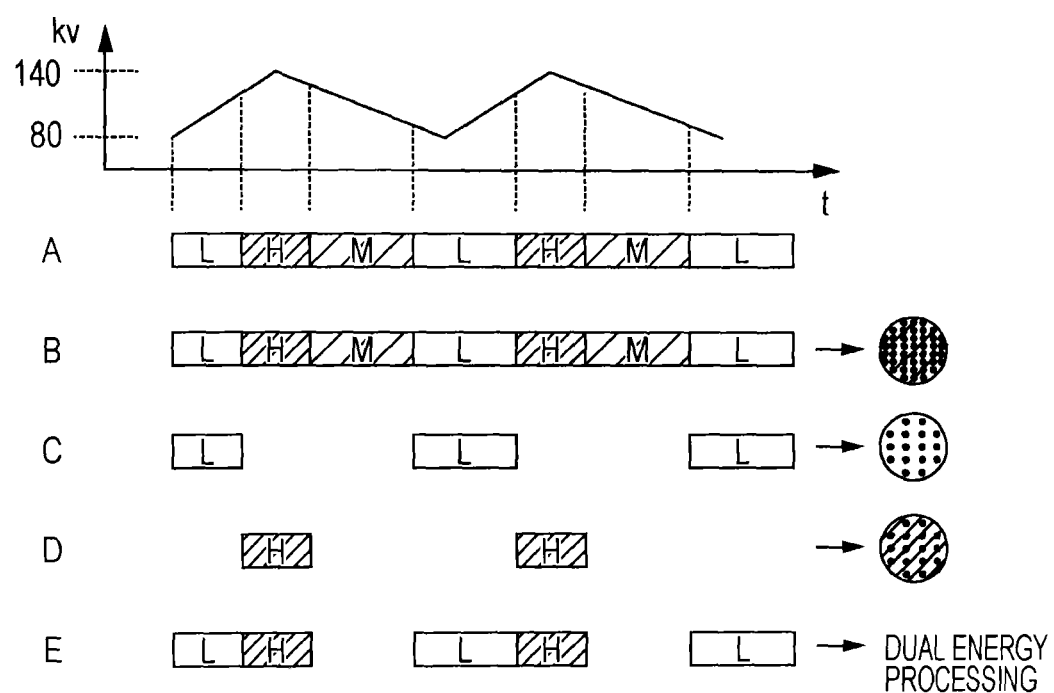
FIG. 5 is an image respectively showing an example in which the change in tube voltage becomes a triangle wave, data accumulation example A, image reconstruction examples B to D, and decomposition process example E.

As shown in example A of FIG. 5, the system controller 110 controls the high voltage generator 109 so as to periodically alternate the tube voltage per 1 view by transmitting the prepared triangle waves to the high voltage generator 109 and controls the DAS 104 so as to accumulate the second sampling data after the predetermined amount of time (open period) has past by transmitting control signals for instructing data accumulation to the DAS 104 thereby accumulating the first sampling data within 1 cycle by synchronizing with the change in tube voltage.

Furthermore, the system controller 110 controls the DAS 104 so as to accumulate the third sampling data within the open period.

Furthermore, even though a case of carrying out data accumulation 3 times in 1 cycle was exhibited, this may be carried out 4 times or more. Furthermore, accumulations expressed as "H," "L," and "M" may be respectively assigned to each trial.

(Image Processing)

Next, image processing using the data accumulated by the DAS 104 is described with reference to FIG. 5. FIG. 5 is an image respectively showing image reconstruction examples B to D, along with decomposition process example E.

The image reconstruction examples B to D and the decomposition process example E shown in FIG. 5 are the same as the image reconstruction examples described in Embodiment 1.

Specifically, as shown in examples B to E of FIG. 5, the reconfiguration device 114 reconstructs tomographical images using each from among the first sampling data to the third sampling data. Furthermore, the reconfiguration device 114 reconstructs tomographical images using the second sampling data. Furthermore, the reconfiguration device 114 reconstructs tomographical images using the first sampling data. Furthermore, the reconfiguration device 114 carries out dual energy processing using the first sampling data and the second sampling data. Moreover, the effect of the abovementioned image reconstruction examples B to D, along with decomposition process example E are the same as the image reconstruction examples, etc. described in Embodiment 1; therefore, descriptions thereof are abbreviated.

According to the abovementioned Embodiment 2, in the example in which the change in tube voltage becomes triangle waves, when photographing with a plurality of energies, both dual energy processing and high resolution may be achieved even when the rotation speed is fast.

Furthermore, according to the abovementioned Embodiment 2, the following are advantages of dual energy processing.

Upon image reconstruction, substances are analyzed (separated) based on the data accumulated when a high voltage is applied and the data accumulated when a low voltage is applied to the X-ray tube. Thereby, sufficient resolution may be obtained along with high resolution tomographical images. Furthermore, in order to obtain high resolution, the data is sufficiently large to ensure stable separation regarding energy separation between a high voltage and a low voltage in each view.

Figure 6:
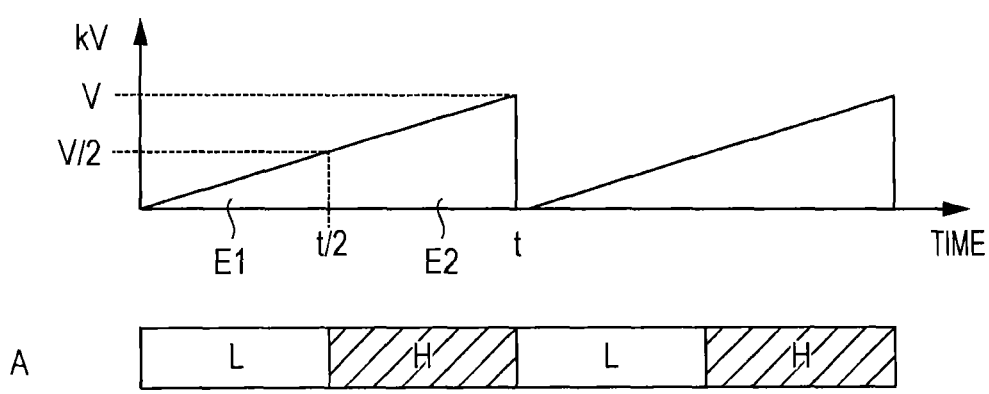
FIG. 6 is an image when both the high voltage and low voltage data are continuously accumulated.
Figure 7:
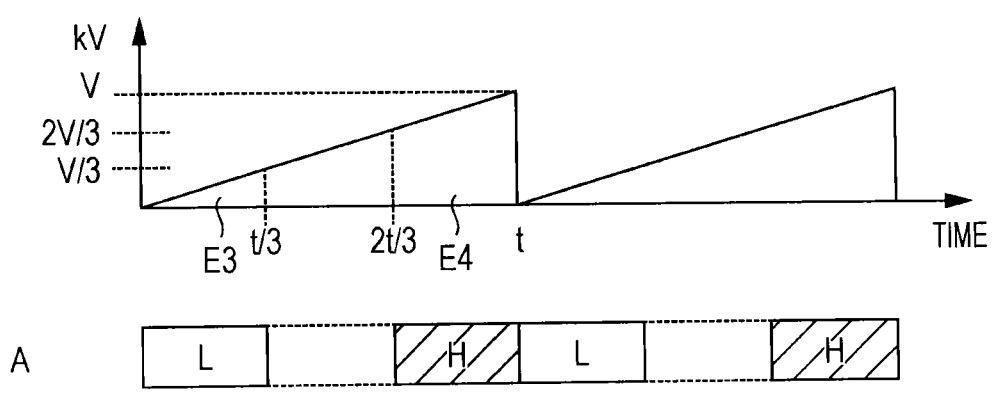
FIG. 7 is an image when both the high voltage and low voltage data are accumulated after a certain interval.

FIG. 6 is an image when both the high voltage and low voltage data are continuously accumulated within 1 cycle by synchronizing with the change in tube voltage, while FIG. 7 is an image when both the high voltage and low voltage data are accumulated within 1 cycle after a certain interval. FIG. 6 and FIG. 7 indicate time [t] on the horizontal axis and voltage [kV] on the vertical axis, and in the example (A), the respective high voltage and low voltage data accumulation examples are shown as "H" and "L." Furthermore, a tube current I is standardized. Moreover, the energy is exhibited as an average voltage (V)*time within the sampling period.

As shown in FIG. 6, when both sets of data are continuously accumulated, the two energies at low and high voltages $E1$ and $E2$ are expressed by $E1=V*t/8$ and $E2=3V*t/8$. At this time, the energy ratio ($E2/E1$) becomes 3/1.

As shown in FIG. 7, when both sets of data are continuously accumulated, the two energies at low and high voltage $E3$ and $E4$ are expressed by $E3=V*t/18$ and $E4=5V*t/18$, respectively. At this time, the energy ratio ($E4/E3$) becomes 5/1.

That is, when both sets of data are continuously accumulated, compared to when they are accumulated after a certain interval, the energy separation is insufficient in each view, causing a decline in the substance separation precision in dual energy processing.

In contrast, when the two sets of data are accumulated after a certain interval, compared to when they are continuously accumulated, the energy separation is sufficient in each view, thereby eliminating the cause of declined substance separation precision in dual energy processing.

Accordingly, even when the two sets of data are accumulated after a certain interval, there is a higher possibility of enhancing substance separation precision compared to when they are continuously accumulated even when the rotation speed is fast.

As mentioned above, according to Embodiment 2, the predetermined amount of time (open period) was provided within 1 cycle; therefore, the energy separation becomes larger in each view, allowing the substance separation precision to be enhanced.

Furthermore, Embodiment 2 showed a case of accumulating data photographed with 3 types of energies; however, the first sampling data and the second sampling data alone may be accumulated without accumulating the data photographed with medium energy (third sampling data). At this time, the amount of time for accumulating third sampling data becomes a predetermined amount of time (open period); therefore, as mentioned above, the predetermined amount of time (open period) was provided in data accumulation, so the data of said area is excluded, thereby enhancing substance separation precision. Furthermore, this configuration and effect is the same regarding the following embodiment.

Embodiment 3

Next, Embodiment 3 is described with reference to FIG. 8 and FIG. 9. Furthermore, in Embodiment 3, configurations differing from Embodiment 1 or 2 are described, and descriptions of the same configuration are abbreviated.

Figure 8:
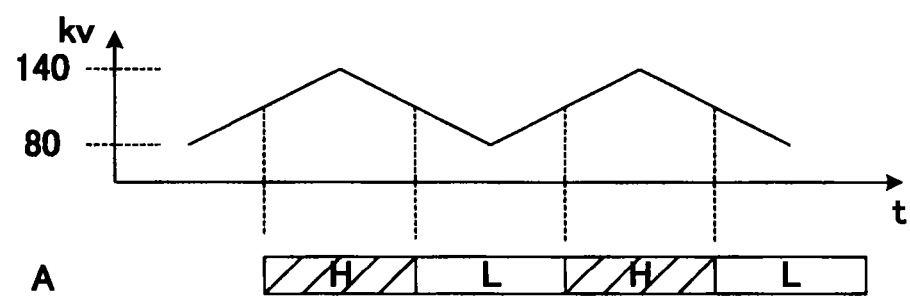
FIG. 8 is an image respectively showing another example in which the change in tube voltage becomes a triangle wave and a data accumulation example regarding the comparative example.

FIG. 8 is an image respectively showing another example in which the change in tube voltage becomes a triangle wave and data accumulation example A regarding the comparative example.
(Data Accumulation)

As shown in FIG. 8, in the data accumulation within 1 cycle, the first sampling data accumulation "H" and the second sampling data accumulation "L" are consecutive.

In comparison, data accumulation is carried out in the following manner in Embodiment 3. FIG. 9 is an image respectively showing an example in which the change in tube voltage becomes a triangle wave and data accumulation example A. In the example A of FIG. 9, the high voltage, low voltage, and medium voltage data accumulation are indicated as "H," "L," and "M."

Figure 9:
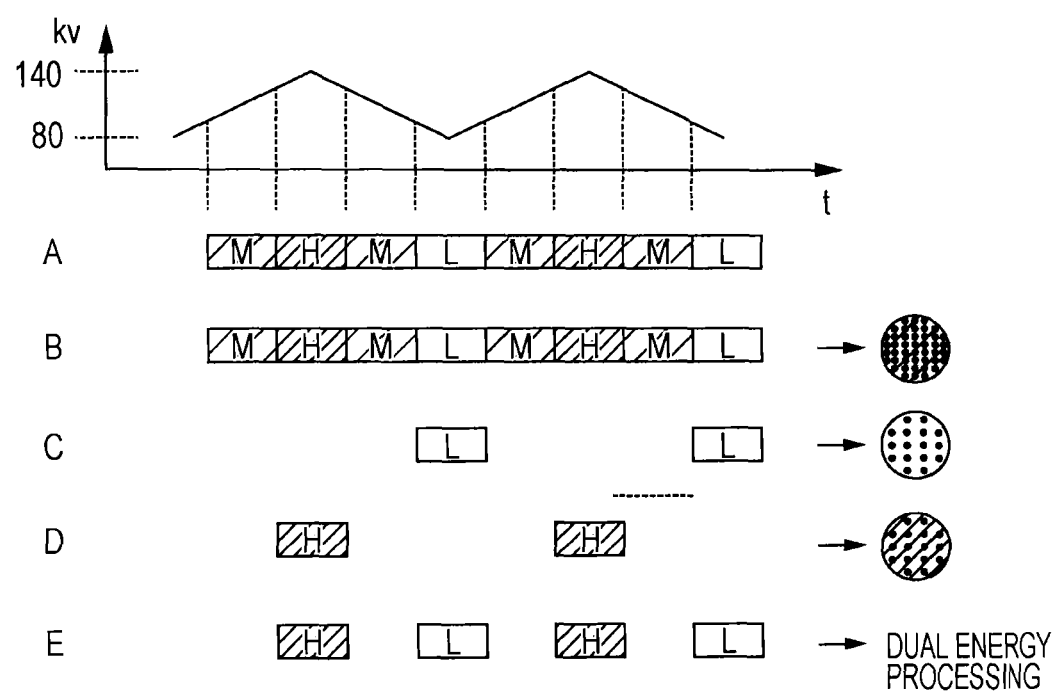
FIG. 9 is an image respectively showing another example in which the change in tube voltage becomes a triangle wave, data accumulation example A, image reconstruction examples B to D, and a decomposition process example regarding Embodiment 3.

As shown in example A of FIG. 9, the system controller 110 controls the high voltage generator 109 such that the tube voltage periodically alternates each 1 view by transmitting the prepared triangle waves to the high voltage generator 109 and controls the DAS 104 so as to accumulate the first sampling data within 1 cycle by synchronizing with the change in tube voltage and accumulating the second sampling data after a predetermined amount of time (open period) has passed after said accumulation, and two predetermined amounts of time are provided within 1 cycle by transmitting control signals for instructing data accumulation to the DAS 104.

Furthermore, the system controller 110 controls the DAS 104 so as to accumulate the third sampling data within the open period.

Furthermore, even when a case of carrying out data accumulation 3 times in 1 cycle was exhibited, this may be carried out 4 times or more. Furthermore, accumulations expressed as "H," "L," and "M" may be respectively assigned to each trial.
(Image Processing)

Next, image processing using the data accumulated by the DAS 104 is described with reference to FIG. 9. FIG. 9 is an image respectively showing image reconstruction examples B to D, along with decomposition process example E.

The image reconstruction examples B to D as well as the decomposition process example E shown in FIG. 9 are the same as the image reconstruction examples shown in Embodiments 1 and 2.

That is, as shown in examples B to E of FIG. 9, the reconfiguration device 114 reconstructs tomographical images using each from among the first sampling data to the third sampling data. Furthermore, the reconfiguration device 114 reconstructs tomographical images using the second sampling data. Furthermore, the reconfiguration device 114 reconstructs the tomographical images using the first sampling data. Furthermore, the reconfiguration device 114 carries out dual energy processing using the first sampling data and the second sampling data. Moreover, the effect of the abovementioned image reconstruction examples B to D, along with decomposition process example E are the same as the image reconstruction examples described in Embodiments 1 and 2; therefore, descriptions thereof are abbreviated.

According to the abovementioned Embodiment 3, in the example in which the change in tube voltage becomes a triangle wave, when photographing with a plurality of energies, both dual energy processing and high resolution may be achieved even when the rotation speed is fast.

Furthermore, according to Embodiment 3, two predetermined amounts of time (open period) were provided within 1 cycle, so the energy separation becomes larger in each view, allowing the substance separation precision to be enhanced.

[Oversampling and Bundling]

The abovementioned Embodiments 1 to 3 show a case of accumulating (outputting) data more than three times within 1 cycle.

However, in the data accumulation according to Embodiments 1 to 3, oversampling may be carried out, bundling may be further carried out, and data output may be carried out after said bundling is carried out. Here, data output after bundling is carried out becomes accumulated data.

Next, oversampling and bundling is described with reference to FIG. 10 and FIG. 11. Oversampling refers to sampling data within a cycle shorter than the data cycle by two times or more. Oversampling and bundling of the raw data is carried out by the DAS 104, while the oversampling and bundling of the projected data is carried out by the pre-treatment unit 106.

Figure 10:
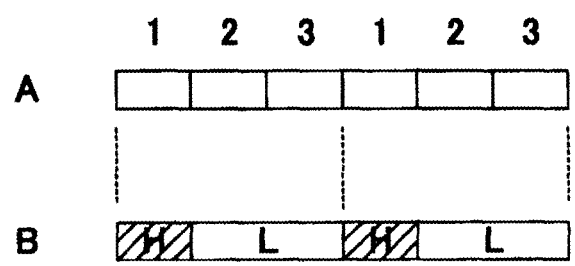
FIG. 10 is an image showing an example of oversampling and bundling.

FIG. 10 is an image respectively showing oversampling example A and bundling example B. The example A shown in FIG. 10 shows the three oversamplings carried out within 1 cycle, while in the example B shown in FIG. 10, bundling of the second and third oversampling is carried out, and the data accumulation "L" is carried out after said bundling is carried out.

Figure 11:
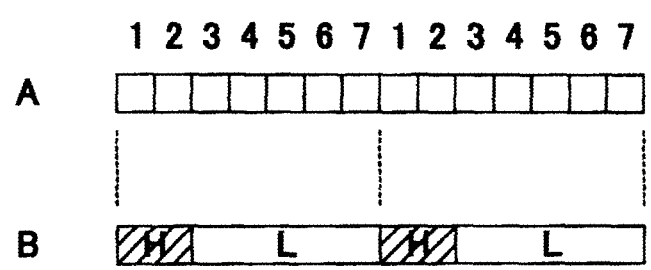
FIG. 11 is an image showing another example of oversampling and bundling.

FIG. 11 is an image respectively showing oversampling example A and bundling example B. In the example A shown in FIG. 11, seven oversamplings carried out within 1 cycle are shown, while in the example B shown in FIG. 11, bundling of the first and second oversampling is carried out, and data accumulation "H" is carried out after said bundling is carried out. Moreover, bundling of the third to seventh oversamplings is carried out, and the data accumulation "L" is carried out after said bundling is carried out.

Embodiment 4

Next, Embodiment 4 is described with reference to FIG. 12. Furthermore, in Embodiment 4, the configurations differing from the respective embodiments of Embodiments 1 to 3 are mainly described, with descriptions on the same configuration abbreviated.

In this embodiment, the reconfiguration device 114 extracts the part of data respectively accumulated when a high voltage and a low voltage are applied from the data accumulated by means of the oversampling.

FIG. 12 is an image respectively showing an example in which the change in tube voltage becomes a triangle wave, a storing example of all oversampled data A, comparative bundling example B, and a bundling example C. Regarding the example of tube voltage change shown in FIG. 12, time [t] on the horizontal axis and voltage [kV] on the vertical axis are indicated.

The example A FIG. 12 shown in FIG. 12 shows eight oversamplings carried out within 1 cycle.

In the comparative example B shown in FIG. 12, bundling of the first to fourth oversamplings is carried out, and data accumulation "H" is carried out following said bundling. Moreover, bundling of the fifth and eighth oversamplings is carried out, and data accumulation "L" is carried out following said bundling. In the comparative example B, the bundling of the first to fourth is considered to be "H" and the bundling of the fifth to eighth is considered to be "L". The further processing is executed based on matters described above.

In contrast, in the example C shown in FIG. 12, bundling of the second and third oversamplings is carried out, and data accumulation "H" is carried out following said bundling. Moreover, bundling of the sixth and seventh oversamplings is carried out, and data accumulation "L" is carried out following said bundling. In the comparative example C, the bundling of the second and third is considered to be "H" and the bundling of the sixth and seventh is considered to be "L". The further processing is executed based on matters described above.

In the comparative example B shown in FIG. 12, the data accumulation "H" and data accumulation "L" are continuously carried out.

In contrast, in the example C shown in FIG. 12, the data accumulation "H" and the data accumulation "L" are accumulated after a predetermined time (time corresponding to the $4^{th}$ and $5^{th}$ oversampling) has past.

According to the abovementioned Embodiment 4, when photographing with a plurality of energies, both dual energy process and high resolution may be achieved even when the rotation speed is fast.

Furthermore, according to Embodiment 4, by means of storing all oversampled data and appropriately bundling the data, the predetermined time (spare time) was provided within 1 cycle of data accumulation; therefore, substance separation accuracy in the dual energy process may be enhanced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of embodiments described herein may be made without departing from the spirit of the inventions. The accompanying claims and their equivalents are intended to cover such forms or modifications as would fall within the scope and spirit of the inventions.

What is claimed is:

1. An X-ray CT device, comprising:
an X-ray tube,
a tube voltage generator adding tube voltage to the X-ray tube,
a tube voltage controlling unit controlling the tube voltage generator so as to periodically alternate said tube voltage,
an X-ray detector detecting the X-rays penetrating the subject,
a data accumulating unit that accumulates first sampling data when a high voltage is applied to the X-ray tube in one cycle synchronizing with a change in the tube voltage from data detected by the X-ray detector, accumulates second sampling data when a low voltage is applied to the X-ray tube in the one cycle from data detected by the X-ray detector after a predetermined amount of time has passed from an end of the accumulation of the first sampling data, and accumulates third sampling data at least once when a medium voltage is applied to the X-ray tube within the predetermined amount of time, from the data detected by the X-ray detector, and an image processing unit that creates an image by reconstructing sampling data over multiple views based on the accumulated first sampling data, the accumulated second sampling data, and the accumulated third sampling data.

2. The device according to claim 1, wherein the image processing unit carries out dual energy processing including substance separation and preparation of a single-colored image using the accumulated first sampling data and the second sampling data.

3. The device according to claim 1, wherein the data accumulating unit carries out oversampling when the high voltage and the low voltage are applied during the one cycle to generate oversampled data, and the image processing unit extracts a part of the oversampled data respectively accumulated when the high voltage and the low voltage are applied.

* * * * *